(12) United States Patent
Jeffery et al.

(10) Patent No.: US 6,254,779 B1
(45) Date of Patent: Jul. 3, 2001

(54) TREATMENT OF EFFLUENT STREAMS CONTAINING ORGANIC ACIDS

(75) Inventors: Ian Charles Jeffery; Christopher Howard Jackson, both of Cleveland (GB)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/380,423

(22) PCT Filed: Mar. 5, 1998

(86) PCT No.: PCT/GB98/00740

§ 371 Date: Feb. 11, 2000

§ 102(e) Date: Feb. 11, 2000

(87) PCT Pub. No.: WO98/41478

PCT Pub. Date: Sep. 24, 1998

(30) Foreign Application Priority Data

Mar. 14, 1997 (GB) .................................................. 9705349

(51) Int. Cl.$^7$ ................................. C02F 3/02; C02F 1/58; C07C 51/16; C07C 51/42
(52) U.S. Cl. .......................... 210/620; 210/631; 210/639; 210/652; 210/758; 210/763; 210/195.2; 210/195.3; 210/205; 210/908; 562/405; 562/407; 562/494; 562/513
(58) Field of Search .................................... 210/605, 610, 210/620, 631, 639, 649, 758–763, 195.2, 630, 195.3, 749, 201, 202, 205, 757, 908, 909, 500.21, 650, 651, 652; 562/405, 407, 494, 513

(56) References Cited

U.S. PATENT DOCUMENTS

| | | | |
|---|---|---|---|
| 2,444,527 | * | 7/1948 | Pomeroy . |
| 2,461,740 | * | 2/1949 | Kiebler . |
| 2,786,074 | * | 3/1957 | Goren . |
| 4,017,421 | * | 4/1977 | Othmer . |

(List continued on next page.)

FOREIGN PATENT DOCUMENTS

| | | |
|---|---|---|
| 0498591B1 | 4/1995 | (EP) . |
| 0502628B1 | 10/1996 | (EP) . |
| WO 93/24440 | 12/1993 | (WO) . |
| WO 96/39595 | 12/1996 | (WO) . |
| WO 97/30963 | 8/1997 | (WO) . |

OTHER PUBLICATIONS

Derwent Patent Abstract of Japan, 1989–019416, 19881201.
Derwent Patent Abstract of Japan, 1994–237852, 19940621.
Derwent Patent Abstract of Japan, 1985–233044, 19850808.

*Primary Examiner*—David A. Simmons
*Assistant Examiner*—Fred Prince
(74) *Attorney, Agent, or Firm*—Charles E. Krukiel

(57) ABSTRACT

An acidic organics-containing waste water stream (12) derived from for example plant for the production of an aromatic carboxylic acid such as terephthalic acid is treated to allow recovery of alkali and water for recycle to the production process. The treatment comprises adjusting the pH of the waste water stream using an alakaline medium, oxidising (10) the organics content of the stream to convert the same to water, carbon dioxide and (bi)carbonate ions, and supplying the treated stream to a reverse osmosis membrane (28, 30) to produce a retentate containing (bi) carbonate ions and cations derived from the alkaline medium and a permeate which is substantially free of those components. The retentate (46) is recycled for use in adjustment of the pH of the waste water stream and, if desired, water-consuming facilities which can tolerate less pure water. The permeate (44) may also be recycled, with or without further treatment, for use in water-consuming facilities within and/or associated with the production plant.

13 Claims, 2 Drawing Sheets

U.S. PATENT DOCUMENTS

| | | | |
|---|---|---|---|
| 4,282,323 | * | 8/1981 | Yates . |
| 4,339,596 | * | 7/1982 | Coffey et al. . |
| 4,345,098 | * | 8/1982 | Schep . |
| 4,604,214 | * | 8/1986 | Carr et al. . |
| 5,028,336 | * | 7/1991 | Bartels et al. . |
| 5,154,836 | * | 10/1992 | Clough . |
| 5,395,497 | * | 3/1995 | Bourgeois . |
| 5,478,472 | * | 12/1995 | Dilla et al. . |
| 5,547,583 | * | 8/1996 | Alexander . |
| 5,766,439 | * | 6/1998 | Eyal et al. . |
| 5,848,363 | * | 12/1998 | Guillermier et al. . |
| 5,859,262 | * | 1/1999 | Eyal et al. . |
| 6,001,255 | * | 12/1999 | Eyal et al. . |

* cited by examiner

TREATMENT OF EFFLUENT STREAMS CONTAINING ORGANIC ACIDS

This invention relates to the treatment of effluent streams containing an organic acid species, e.g. the treatment of effluent arising from the production of aromatic carboxylic acids.

According to one aspect of the present invention there is provided a process for the treatment of an effluent stream containing water and an organic acid species which is a stronger acid than carbonic acid, comprising:

adding an alkaline medium to increase the pH of the effluent stream;

subjecting the effluent stream to oxidation treatment to convert the organic acid species to carbon dioxide, water and carbonate and/or bicarbonate ions;

separating the oxidised effluent stream into a concentrated aqueous stream rich in (bi)carbonate ions and cationic species derived from said alkaline medium and a depleted aqueous stream which is substantially free of said (bi) carbonate ions and said cationic species; and recycling the concentrated stream for direct or indirect use as said alkaline medium.

Preferably the separation of the oxidised stream into said concentrated and depleted streams is effected by means of at least one reverse osmosis membrane. However, we do not exclude the possibility of carrying out this separation by other suitable means using for instance an evaporative technique such as multi-effect evaporation.

Typically the alkaline medium contains alkali metal or ammonium cations. Recycling of the concentrated stream allows the alkali metal/ammonium to be repeatedly recycled within the process and substantial savings may be secured since the consumption of alkaline medium, e.g. caustic soda, can be reduced significantly.

The oxidation stage may take various forms such as biological digestion, wet oxidation (e.g. Loprox or Zimpro wet oxidation processes), chemical oxidation (e.g. treatment with oxidising agents such as ozone and/or peroxide with or without the use of radiation such as ultra-violet light) and any combination of two or more of these treatment techniques.

The alkaline medium may be added prior to and/or during said oxidation step.

Prior to contacting the oxidised effluent stream with the reverse osmosis membrane or the like, the stream is preferably subjected to one or more stages of solids-liquid separation in order to reduce or eliminate any particulate matter that may be suspended in the effluent stream. Usually such solids-liquid separation is effected prior to separation of the the oxidised effluent stream into said concentrated and depleted streams.

In a more specific application thereof the invention relates to the treatment of an effluent stream or streams arising from the production of aromatic carboxylic acids, such as terephthalic acid and isophthalic acid.

Terephthalic acid for example is produced commercially by oxidising p-xylene with oxygen in a liquid phase which comprises a lower aliphatic carboxylic acid solvent, such as acetic acid, and a dissolved heavy metal catalyst system (usually cobalt and manganese and a bromine promoter). A slurry of terephthalic acid in the solvent is withdrawn from the reactor and is subjected to a solids-liquid separation process resulting in crude terephthalic acid crystals which may be subsequently processed further and a mother liquor filtrate which, in addition to catalyst and promoter used in the oxidation reaction, contains dissolved terephthalic acid and various by-products and impurities. These by-products and impurities arise from various sources such as minor impurities in the p-xylene feed stock to the reaction, incomplete oxidation of p-xylene resulting in partially oxidised products and by-products arising from the competing side reactions in the oxidation of p-xylene to terephthalic acid.

It is common practice to recycle a large proportion of the recovered mother liquor to the oxidation reaction in order to return catalyst and promoter to the oxidation reaction while purging a smaller proportion to a solvent recovery system so as to maintain the level of impurities and by-products in the reaction within tolerable limits. In the solvent recovery system, the mother liquor purge is subjected to evaporation to remove a substantial proportion of the aliphatic acid solvent present (which can be returned to the oxidation reaction) and water leaving a concentrate containing terephthalic acid and impurities/by-products together with some of the heavy metal catalyst present in the original mother liquor filtrate. The concentrate (the residues) may then be disposed of or, if economically justifiable, treated in order to recover valuable components for recycling, e.g. catalyst metals. Typical downstream treatments of the residues include catalyst recovery, incineration and anaerobic/aerobic biological treatment to reduce chemical oxygen demand (COD).

The terephthalic acid obtained from the liquid phase oxidation reaction usually contains impurities at levels which are unacceptable for subsequent uses of the acid, e.g. polyester fibre production. For instance, crude terephthalic acid produced in this way typically contains impurities such as 4-carboxybenzaldehyde (4-CBA), which tends to co-precipitate with terephthalic acid, and so-called colour bodies. To reduce the impurities to acceptable levels, it is well known to purify crude terephthalic acid by dissolving the same in an aqueous medium and then contacting the solution with hydrogen in the presence of a suitable hydrogenation catalyst. Such a purification process is described in our prior European Patent Applications Nos. 498591 and 502628, the entire disclosures of which is incorporated herein by this reference. In the process of EP-A-498591 and EP-A-502628, following reaction with hydrogen (which serves to convert 4-CBA to paratoluic acid and the so-called colour bodies to other non-coloured species), the solution undergoes crystallisation resulting in a slurry comprising crystals of purified terephthalic acid in aqueous mother liquor. The purified terephthalic acid is then recovered by solids-liquid separation as disclosed for instance in our prior International Patent Application No. WO 93/24440, the entire disclosure of which is incorporated herein by this disclosure. At least part of the recovered aqueous mother liquor (pure plant mother liquor) may be recycled within the process as described in EP-A-498591 so that use can be made of its water content and also its organic content, including terephthalic acid precursors such as paratoluic acid. Such recycle is effected by passing the mother liquor (with or without intervening treatment) to a distillation column associated with the oxidation reaction and used for separating water from aliphatic carboxylic acid solvent. At least part or substantially all of the pure plant mother liquor may be passed to effluent treatment plant. Conventional practice has been to discard all of the pure plant mother liquor.

As applied to the production of an aromatic carboxylic acid such as terephthalic acid and isophthalic acid, one aspect of the process according to the invention comprises feeding at least one organic acid-containing waste water stream generated in the course of operating the process to a waste water treatment plant in which the pH of the stream is adjusted by the addition of an alkaline medium and is subjected to oxidation treatment to decompose its organic components, separating the oxidised stream into a depleted stream comprising water having low organics content and a concentrated stream comprising water from said stream, cationic species derived from the alkaline medium and (bi)carbonate ions generated in the course of oxidation of the organics, at least part of the concentrated stream being recycled for use in said adjustment of the pH of the waste water stream and, optionally, at least part of the depleted stream being recovered and re-used in one or more water-consuming applications within and/or associated with the production process.

A feature of the process of the present invention is that water-containing effluent streams from an aromatic carboxylic production process can be managed in such a way as to allow significant reduction in the importation of raw water into the production process, in contrast with conventional plant where substantial quantities of raw water are imported for demineralisation and use in the process and where waste water streams are discharged in their entirety following treatment to reduce COD content.

Thus, for example, the recovered depleted stream as such and/or after treatment may be re-used in one or more parts of the plant for the production of the aromatic carboxylic acid, including water-consuming/steam generating utilities associated with the plant. Typical uses of the recovered water include wash liquor duties for washing aromatic carboxylic acid crystals recovered for example in the form of a filter cake in the course of the pure solids-liquid separation; high and low pressure seal water on pumps and agitators; scrubbing duties; offgas desuperheating; steam make-up; dilution of concentrated alkali metal hydroxide (e.g. caustic soda); and resin regeneration and blowdown in water demineralisation plant.

The reference above and elsewhere in this patent specification to "re-use" in one or more parts of the production process is to be understood to encompass use of recovered water in core parts of the plant involving the oxidation reaction and/or the purification reaction as well as ancillary parts of the plant such as treatment of the offgas from the oxidation reaction, recovery of catalyst metals etc.

Preferably before re-use in the process, at least part (usually at least the major part) of the depleted stream is treated further to reduce the impurity content to a level compatible with the re-use to which it is to be put. The depleted stream may for instance be split into different fractions which are processed differently according to needs. For example, some of the depleted stream obtained may be used directly, without further purification, for applications which can tolerate the impurity level within the untreated depleted stream. Another fraction or fractions may be purified in any suitable manner, for instance by processing in a demineralising plant or by subjecting the depleted stream or part thereof to one or more further stages of treatment using a reverse osmosis membrane or membranes or the like, it being understood that where more than one further stage is employed, at least part of the depleted stream derived from each stage but the last will be passed for treatment to the next stage. Part of the interstage water recovered may be diverted for use in any part of the production process in which water of that quality can be tolerated. In this manner, it is possible to obtain a number of water streams of different qualities, each compatible with a particular process requirement.

The waste water treatment plant preferably comprises an oxidation stage in which the feed stream is subjected to oxidising conditions to effect conversion of organic acid species therein to carbon dioxide, water and (bi)carbonate ions, the pH of the feed stream being adjusted to reduce its acidity by the addition of an alkaline medium containing ammonium or more usually an alkali metal.

Typically the waste water will constitute a source of the alkali metal resulting in a depleted stream containing potassium or sodium and (bi)carbonate ions. The sodium or potassium content in the waste water stream or streams for instance arises from the use of aqueous caustic soda or potassium hydroxide in one or more duties within the production process. For example, caustic soda solution is usually used for caustic washing of various plant components such as equipment for filtering, cooling and flashing down of pure plant mother liquor, belt filtration equipment for use in effecting aliphatic carboxylic acid/water solvent exchange as described in EP-A-502628 (e.g. caustic washing of the return run of the filter band), and equipment for evaporating aliphatic carboxylic acid solvent from the residues obtained from treatment of a purge taken from a mother liquor recycle to the oxidation zone from solids-liquid equipment associated with the liquid phase oxidation. Caustic soda solution may also be employed in other duties such as caustic scrubbing of offgas derived from the oxidation reactor, e.g. following catalytic oxidation thereof and power recovery by passage through an expander as described in International Patent Application No. WO 96/139595.

According to another aspect of the present invention there is provided a process for the production of an aromatic carboxylic acid, comprising:

effecting liquid phase oxidation of a precursor of said aromatic carboxylic acid in an aliphatic carboxylic acid solvent in the presence of a heavy metal catalyst system;

supplying a slurry of the resulting aromatic carboxylic acid crystals in solvent-based mother liquor to a solids-liquid separation section to separate said crystals of crude aromatic carboxylic acid from said solvent-based mother liquor;

dissolving the crude acid crystals in aqueous medium;

hydrogenating the resulting solution to reduce the impurity content of the aromatic carboxylic acid;

separating purified crystals of the aromatic carboxylic acid from aqueous-based mother liquor;

adjusting the pH of at least part of the aqueous-based mother liquor by the addition of alkaline medium thereto;

following pH adjustment subjecting said aqueous-based mother liquor in treated or untreated form to an organics digestion process to produce a reduced COD aqueous stream containing suspended solids and dissolved species including (bi)carbonate ions and cationic species derived from said alkaline medium;

processing said reduced COD aqueous stream to separate the same into a concentrated stream comprising a minor fraction of the water from said reduced COD aqueous stream and containing substantially all of the impurities constituted by said dissolved species, including (bi)carbonate ions, and a depleted stream which comprises a major fraction of the water from the reduced COD stream and which is substantially free of said impurities; and recycling at least part of said depleted stream for direct or indirect use in said pH adjustment and, optionally, recycling at least part of the depleted stream for re-use in one or more water-consuming units within and/or associated with the production plant.

The aqueous-based mother liquor typically constitutes the major waste water stream supplied to the organics digestion stage and may be in treated or untreated form. Where such treatment is applied, it may comprise processing to precipitate further solids in the form of less pure crystals of the aromatic carboxylic acid and intermediates such as paratoluic acid in the case of terephthalic acid, which solids may be recycled to the oxidation zone.

Where the oxidation stage employs biological digestion, the concentrated stream containing alkali metal and (bi)carbonate ions is conveniently added to the process waste water streams (which, collectively, form an acidic aggregate) in order to increase the pH thereof for compatability with the biological digestion process. Recycling of the concentrated stream to the digestion stage affords the advantage that any dissolved, unconsumed nutrients originating from the biological digestion stage are thereby recycled to the digestion stage.

The digestion stage receiving the process waste water streams may involve biological digestion under aerobic or anaerobic conditions. Where the digestion stage operates under anaerobic conditions, it is conveniently used in conjunction with an aerobic digestion stage located downstream of the anaerobic stage and upstream of a solids-liquid separation stage in which the reduced COD aqueous stream is separated into a solids-rich stream comprising suspended solids and water from said reduced COD stream and a substantially solids-free stream comprising water and dissolved impurities, the solids-free stream from the solid-liquid separation stage being processed to produce said concentrated and depleted streams. At least part of one or more of the solids-rich stream, the solids-free stream, the concentrated stream and depleted stream may be recycled for re-use in one or more water-consuming applications within and/or associated with the production process.

Typically, recycle of one or more of the various streams mentioned above may involve any one or a combination of the following:

1. recycle of at least part of the solids-rich stream (typically substantially the entire stream) to a thermal oxidiser stage for effecting high temperature oxidation of organics, especially organic residues recovered from the oxidation zone mother liquor purge—for instance, the solids-rich stream may be employed as a quench and/or scrubbing liquor for cooling/scrubbing flue gases produced by the thermal oxidiser since a relatively "dirty" liquor can be tolerated for duties such as these;
2. recycle of part of the substantially solids-free stream for use in the production of a mist/fogging spray in a wet electrostatic precipitator for removal of entrained particulate pollutants present in flue gases before discharge from the thermal oxidiser.
3. recycle of the concentrated stream to the catalyst recovery stage for use as an alkaline agent in aiding dissolution of the residue and/or precipitation of the catalyst metal(s), this being possible since the concentrated stream will usually comprise alkali metal (bi)carbonate;
4. recycle of at least part of the concentrated stream to the organics digestion stage for use in neutralisation of the acid values contained in the waste water streams, especially the aqueous-based mother liquor;
5. recycle of at least part of the concentrated stream to the thermal oxidiser, where employed, for use as an alkaline liquor in the scrubbing of pollutants such as bromine and hydrogen bromide from the flue gases;
6. recycle of at least part of the concentrated stream for use as an alkaline liquor in the removal of pollutants such as bromine and/or hydrogen bromide from offgas derived from the oxidation zone, e.g. following catalytic combustion of the offgas to destroy organics and convert methyl bromide to bromine and/or hydrogen bromide; and
7. recycle of part of the depleted stream for use in quenching the hot offgas from the oxidation zone prior to scrubbing, especially following catalytic combustion of the offgas and also other duties as referred to previously.

The solids-liquid separation stage to which the reduced COD stream is supplied conveniently comprises one or more microfiltration membranes (the term "microfiltration" being used herein to encompass similar forms of filtration such as nanofiltration and ultrafiltration). Preferably the solids-liquid separation stage comprises a microfiltration membrane stage of the cross flow type in which a major part of the liquid permeates through the membrane while the solids suspended in the liquid are entrained in a liquid flow across the upstream face of the membrane.

In one embodiment of the invention the process includes a catalyst recovery stage in which a residue derived from concentrating a purge taken from the mother liquor recycle to the oxidation reactor is processed to yield catalyst metal for recycle to the oxidation reactor. The residue typically contains organics and catalyst metals, e.g. cobalt and/or manganese. In this embodiment, the residue which is predominantly acidic in nature is preferably dissolved in aqueous medium with the aid of initial alkali addition (desirably to dissolve substantially the whole of the residue) followed by further alkali addition to effect precipitation of the catalyst metal(s) as carbonates thereof. The aqueous used for dissolution of the residue is conveniently constituted in part (usually the major part) by said aqueous-based mother liquor before or after treatment thereof. The initial and/or further alkali addition is conveniently effected using one or more alkali metal/(bi)carbonate-containing streams from within the process, for example the concentrated stream referred to above.

The invention will now be described further by way of example with reference to the accompanying drawings in which.

For the purposes of illustration, the following description is given with reference to a process for the production of terephthalic acid by the liquid phase oxidation of paraxylene. However, it is to be understood that the process of the invention is not limited to terephthalic acid production but may be applied to the production of other aromatic carboxylic acids such as isophthalic acid.

Figure 1:
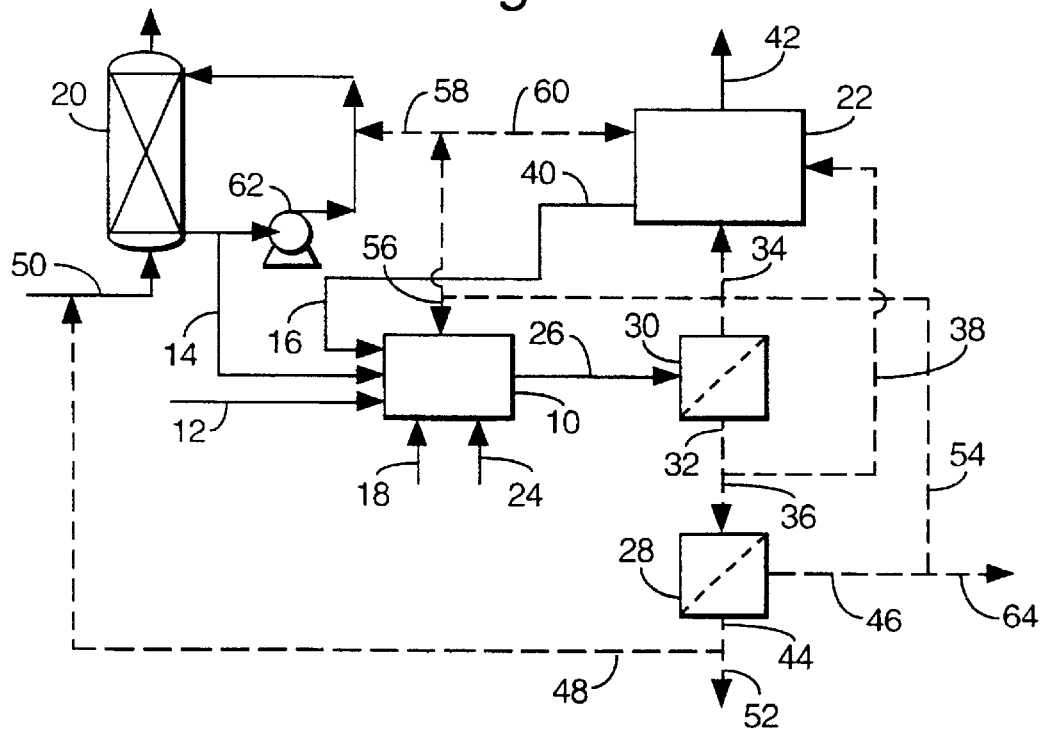
FIG. 1 illustrates one form of effluent treatment plant for use in the processing of waste waters from plant for the production of an aromatic carboxylic acid such as terephthalic acid.

Referring to FIG. 1, this illustrates an effluent treatment scheme comprising an aerobic biological treatment unit 10, an offgas scrubber 20 and a thermal oxidiser. The offgas scrubber 20 forms part of apparatus for the processing the offgas from the oxidation reactor in which the liquid phase oxidation of paraxylene is carried out to produce terephthalic acid. One form of offgas treatment apparatus is described in our copending International Patent Publication No. WO 96/39595, the entire contents of which are incorporated herein by this reference. Thus, the scrubber 20 in FIG. 1 of the present application may correspond to the scrubbing section 30 and/or the scrubbing unit 60 described in International Patent Publication No. WO 96/39595. The thermal oxidiser 22 may be of any suitable form for use in the incineration of primarily organic residues resulting from treatment of an acetic acid-based mother liquor purge derived from the mother liquor recycle conventionally used in the production of crude terephthalic acid. One process for the treatment of the mother liquor recycle and purge is described in International Patent Publication No. WO97/30963 and International Patent Application No. GB97/02158, the entire contents of both applications being incorporated herein by this reference. For the purposes of understanding the present invention, the salient features of the thermal oxidiser operation are those involving the processing of the flue gases resulting from high temperature oxidation of the residues, namely the clean-up of the flue gases by the sequence of quenching/cooling the hot flue gases arising from incineration with water, aqueous venturi scrubbing of the quenched flue gases, caustic scrubbing of the flue gases and finally passage of the scrubbed flue gases through a wet electrostatic precipitator.

The aerobic biological treatment unit 10 receives waste waters supplied via lines 12, 14, 16 and 18 and comprising the following:

line 12—from the purification process, aqueous mother liquor containing dissolved organics such as terephthalic acid, paratoluic acid and acetic acid (pure plant mother liquor);

line 14—from offgas scrubber 20, an aqueous purge stream containing mainly sodium carbonate, sodium bicarbonate, sodium bromide and sodium acetate;

line 16—from thermal oxidiser 22, an aqueous purge stream containing sodium bromide, sodium carbonate and sodium bicarbonate;

line 18—spent caustic wash water employed in washing duties on the plant and containing caustic soda and organic sodium salts such as sodium salts of acetic acid, terephthalic acid and paratoluic acid.

The major component, pure plant mother liquor, is typically derived from the slurry resulting from crystallisation of the hydrogenated solution obtained in the course of purifying terephthalic acid. The slurry is subjected to a solids-liquid separation under elevated temperature and pressure conditions, e.g. 148° C., 4.5 bara, to produce the pure plant mother liquor as filtrate. This filtrate is then flashed down in mother liquor flash drum to about 100° C., 1 bara, cooled to about 50° C. to precipitate solids and filtered to remove solids. The cooled and filtered pure plant mother liquor, containing inter alia acetic acid, terephthalic acid, paratoluic acid, 4-carboxybenzaldehyde and other aromatic organic acids, is then passed to waste water treatment—although at least part of the pure plant mother liquor may be recycled in the process in the manner disclosed in for example EP-A-498591, EP-A-502628 and/or WO 93/24440.

Microbial digestion of the organics in the presence of nutrients takes place in the aerobic treatment unit 10. The nutrients employed typically consist of metal cations such as Fe, Mg, K, and anions such as $SO_4$, $PO_4$, $NO_3$, $NH_4$. Make-up nutrients to compensate for nutrients consumed in the aerobic process and nutrients lost by purging are supplied to the unit 10 via line 24. The output from the aerobic unit 10 comprises an aqueous stream containing suspended solids which may be subjected to settling/clarification and filtration (not shown) to produce an aqueous stream (line 26) containing biomass in the form of suspended solids (typically of the order of 30 ppm), dissolved species including sodium carbonate and bicarbonate (typically of the order of 1500–2000 ppm) and undigested organics and dissolved minerals associated with the nutrients supplied to the aerobic unit 10. The chemical oxygen demand (COD) of the undigested organics and suspended solids typically amounts to 100–250 ppm. In conventional effluent plant, this aqueous stream following settling/clarification and sand filtration would be discharged to drain.

In the embodiment of FIG. 1, the aqueous stream from the aerobic unit 10, following removal of suspended solids by settling/clarification and sand filtration, is passed to a reverse osmosis (RO) membrane separator stage 28 after passage through means for reducing the suspended fine solids content of the aqueous stream, the particle size of the suspended solids typically being of the order of 10 microns. Such means will usually be in the form of a membrane separator stage 30 such as a cross flow microfiltration membrane and is employed so as to reduce the risk of fouling of the RO membrane by suspended fine solids in the aqueous stream (line 26) from the aerobic unit 10. The RO membrane typically comprises a cellulose acetate (e.g. a composite cellulose diacetate and triacetate) membrane or an aromatic polyamide membrane. The separator stage 30 produces an aqueous stream (line 32) which contains dissolved species but is free of fine solids and an aqueous stream (line 34) containing substantially all of the suspended fine solids content of the aerobic output stream (line 26). The stream 32 is split into two fractions, a major fraction 36 which is supplied to the RO membrane separator stage 28 and a minor fraction 38 which is supplied to the thermal oxidiser 22. Typically the fraction 38 will comprise about 3 to 4% wt of the stream 32 from the stage 30 and is employed in a wet electrostatic precipitator as a fogging spray for removing solids from the gas to be vented via line 42 from the thermal oxidiser. The fact that the fraction 38 will contain impurities can be tolerated since the spray will remain in the thermal oxidiser and its impurity content will therefore be subjected to incineration and/or be purged to the aerobic unit 10 via line 40. The "dirty" retentate stream 34 from the microfiltration stage 30 is also supplied to the thermal oxidiser 30 for use as quench water in cooling hot flue gases, prior to venturi scrubbing, caustic scrubbing and wet electrostatic precipitation. Again the impurities in this stream can be tolerated since they will either be incinerated and/or returned to the aerobic unit 10 via line 40.

The stream 36 passes to the RO stage 28 resulting in the production of a permeate stream 44 containing a major fraction of the water content of stream 36 (e.g. of the order of 70 to 90% wt) and a very small proportion of the impurity content thereof and a retentate stream 46 containing a minor fraction of the water content of stream 36 but substantially all of the impurity content thereof (e.g. in excess of 95% wt, typically in excess of 98% wt). In practice, the separation carried out in RO stage 28 may readily achieve water of sufficient quality to allow its use as a substitute for demineralised water in at least one situation where demineralised water usage would normally be considered appropriate. Thus, in FIG. 1, part 48 of the permeate stream 44 is diverted for use in desuperheating the offgas supplied to the scrubber 20 via line 50. The stream 48 may for example constitute about 10 to about 20% wt of the stream 44. That part 52 of the permeate stream 44 which is not recycled for direct re-use in the production process may be passed to plant for demineralising the water. The demineralising plant typically comprises multiple vessels in parallel that enable on-line regeneration of the anion and cation resins by cleaning with HCl/NaOH and backwashing with fresh demineralised water. In principle, the water used in regeneration of the resins can also be recycled to the aerobic unit 10 and recovered via the RO membrane stage 28.

The retentate stream 46 typically comprises about 10% wt of the water in stream 36 but contains a high proportion of the sodium content of the stream 36, primarily in the form of sodium carbonate and/or bicarbonate as a result of contact with $CO_2$ contained in the offgas passing through the scrubber 20 which uses an aqueous alkaline sodium-containing solution (e.g. aqueous sodium hydroxide) as the scrubbing medium and $CO_2$ arising from the oxidation of organic acidic species in the aerobic unit 10. Consequently the retentate stream 46 constitutes a concentrated alkali stream, e.g. similar in sodium ion strength to 2.5% caustic, and as such may be used in duties for which aqueous caustic soda would conventionally be employed. Thus, in the embodiment of FIG. 1, part 54 of the retentate stream 46 is diverted and supplied to the aerobic unit 10, the scrubber 20 and the thermal oxidiser 22 (lines 56, 58 and 60 respectively). The stream 56 to the aerobic unit 10 is employed in neutralisation of the feedstreams to the unit 10 which, when combined, produce an aggregate which is acidic. The stream 58 to the scrubber 20 is employed as make-up in the recirculating loop around which the scrubbing medium is pumped by pump 62 and from which the purge via line 14 is taken. The stream 60 is employed in the caustic scrubbing stage of the thermal oxidiser 22. The retentate 46 will also contain unconsumed nutrients and consequently the recycle of retentate to the aerobic unit 10 via line 54 serves additionally to reintroduce unconsumed nutrients into the unit 10. The remainder of the retentate stream 46 is purged via line 64, e.g. for disposal. While the purge stream 64 will have significantly higher COD concentration than the COD concentration in stream 26, this arises because the water content of the retentate from the RO membrane stage 28 is much reduced (about 10 to 30% wt relative to the water content of the permeate from the RO membrane stage 28). The net effect is that the total amount of COD discharged via purge 64 is considerably less than the case where the whole of the the stream 26 is discharged without the further treatment imparted by the process of the present invention. Calculations show that the total COD discharge per unit time can be reduced by more than 60%. The recycle of COD may permit capital and operating savings in the design of the effluent treatment plant.

In a typical implementation of the scheme illustrated in FIG. 1 in which about 102 te/hour of treated water is obtained from the aerobic unit 10 via stream 26, it is envisaged that the water content of the various streams illustrated will typically be as indicated in Table 1 below.

TABLE 1

| Stream | Water content (te/hr) | Stream | Water content (te/hr) |
|---|---|---|---|
| 26 | 102.7 | 52 | 71.7 |
| 34 | 6.2 | 46 | 9.3 |
| 32 | 95.9 | 54 | 5.6 |
| 36 | 92.9 | 64 | 3.7 |
| 38 | 3.0 | 56 | 0.4 |
| 44 | 83.6 | 58 | 4.3 |
| 48 | 11.9 | 60 | 1.0 |

From the above, it will be seen that a substantial amount of the water in the stream 26 is recovered for re-use either following demineralisation or from locations upstream of the demineralisation plant, the raw water supply to the purified terephthalic acid production process can be reduced markedly coupled with the significant benefits obtained from sodium recovery for duties normally employing aqueous caustic solutions.

In the embodiment of FIG. 1, a settling/clarifying and sand filtration facility is referred to (but not illustrated). In a modification, this facility can be dispensed with and the microfiltration membrane stage may be suitably designed to effect the same function (macro-particle removal) while also removing suspended fine solids.

Figure 2:
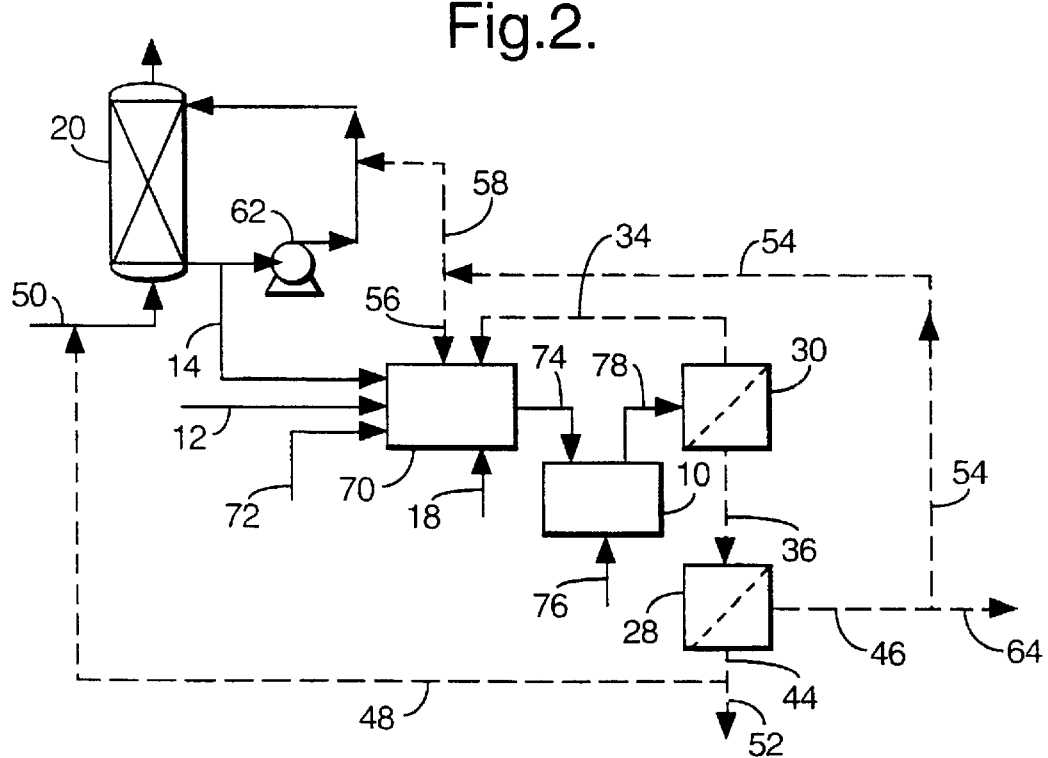
FIG. 2 illustrates a second embodiment of effluent treatment plant employing anaerobic digestion.

Referring now to FIG. 2, this embodiment is similar in many respects to that of FIG. 1 and those parts having similar functions are therefore depicted using the same reference numerals as in FIG. 1. In FIG. 2, the thermal oxidiser is eliminated and the feed streams 12, 14 and 18 are supplied to a facility 70 for effecting catalyst recovery and anaerobically treating the liquid remaining after precipitation of catalyst metals. The process carried out in the facility 70 is described in our copending UK Patent Application No. 9617994.0 filed Aug. 29, 1996, the entire contents of which are incorporated herein by this reference. In outline, the purge taken from the mother liquor recycle to the oxidation reactor is concentrated by evaporation to produce a solid phase residue containing catalyst metals and organics. This residue is supplied via line 72 to the catalyst recovery and anaerobic treatment facility 70 where substantially the whole of the residue is dissolved in an aqueous medium with the inclusion of alkali, e.g. aqueous caustic soda or sodium carbonate and/or bicarbonate, to aid solubilisation. Typically the solubilisation phase involves adjustment of the pH of the acidic liquor to about 5.5. After substantially complete solubilisation has been secured further addition of sodium carbonate and/or bicarbonate is made to precipitate the catalyst metals as carbonates. The aqueous medium is made up mainly of pure plant mother liquor supplied via line 12 and substantially complete solubilisation of the organics and subsequent precipitation of the catalyst metals can be secured by the addition of sodium carbonate and/or sodium bicarbonate derived from sources which are described further below. Following solids-liquid separation of the precipitated catalyst metals, the remaining liquor containing organics is subjected to anaerobic digestion.

The sodium carbonate/bicarbonate employed in the catalyst recovery section of facility 70 is selected from any one or more of the following sources:

stream 14—purge from the scrubber 20;

stream 18—spent caustic wash water employed in washing duties on the plant and containing caustic soda and organic sodium salts such as sodium salts of acetic acid, terephthalic acid and paratoluic acid;

stream 34—retentate from the microfiltration membrane stage 30; and stream 56—from the retentate stream 44 produced by RO stage 28.

The alkalinity of the liquor following catalyst metal precipitation may need to be adjusted to a level appropriate to anaerobic digestion, typically to a pH of about 7 to 8. Where such adjustment requires the addition of alkali, the necessary alkali may be constituted by sodium carbonate and/or bicarbonate derived from any one or more of the above specified sources. Where the adjustment requires acid addition, this may be effected by adding further pure plant mother liquor at this stage. The recycle of sodium for the above purposes is especially beneficial where anaerobic digestion is employed, and even more so where catalyst recovery by carbonate precipitation is practised, because of the otherwise substantial demand for aqueous caustic soda that would be involved in neutralising the acidic pure plant mother liquor to the level required for anaerobic treatment and solubilisation of the catalyst residues.

Following anaerobic digestion, the liquor is passed via line 74 to aerobic digestion unit 10 to which make-up nutrients are supplied via line 76, part of the nutrient requirement being satisfied by recycle of unconsumed nutrient via the retentate from the RO membrane stage 28 via lines 54 and 56. Alternatively, the make-up nutrients may be supplied to the anaerobic digestion stage. The treated stream 78 from the unit 10 is passed to the microfiltation membrane stage 30 and then to RO membrane stage 28. A macrofiltration stage, e.g. settler/clarifier and sand filter, may be associated with the unit 10 or the microfiltration membrane stage 30 may be designed to perform both forms of solids-liquid separation, i.e. macrofiltration and microfiltration. In this embodiment, the retentate 34 from the microfiltation membrane stage 30 is returned directly to the facility 70. The retentate 46 from the RO membrane stage 28 is in part purged via line 64 and in part recycled to the scrubbing loop via line 58 and to the facility 70 via line 56.

In a typical implementation of the scheme illustrated in FIG. 2 in which about 106 te/hour of treated water is obtained from the facility 70 via stream 74, it is envisaged that the water content of the various streams illustrated will typically be as indicated in Table 2 below.

TABLE 2

| Stream | Water content (te/hr) | Stream | Water content (te/hr) |
| --- | --- | --- | --- |
| 74 | 106.7 | 52 | 74.5 |
| 78 | 106.7 | 46 | 9.6 |
| 34 | 10.7 | 54 | 8.0 |
| 36 | 96.0 | 64 | 1.6 |
| 38 | 3.0 | 56 | 6.1 |
| 44 | 86.4 | 58 | 1.9 |
| 48 | 11.9 | | |

Figure 3:
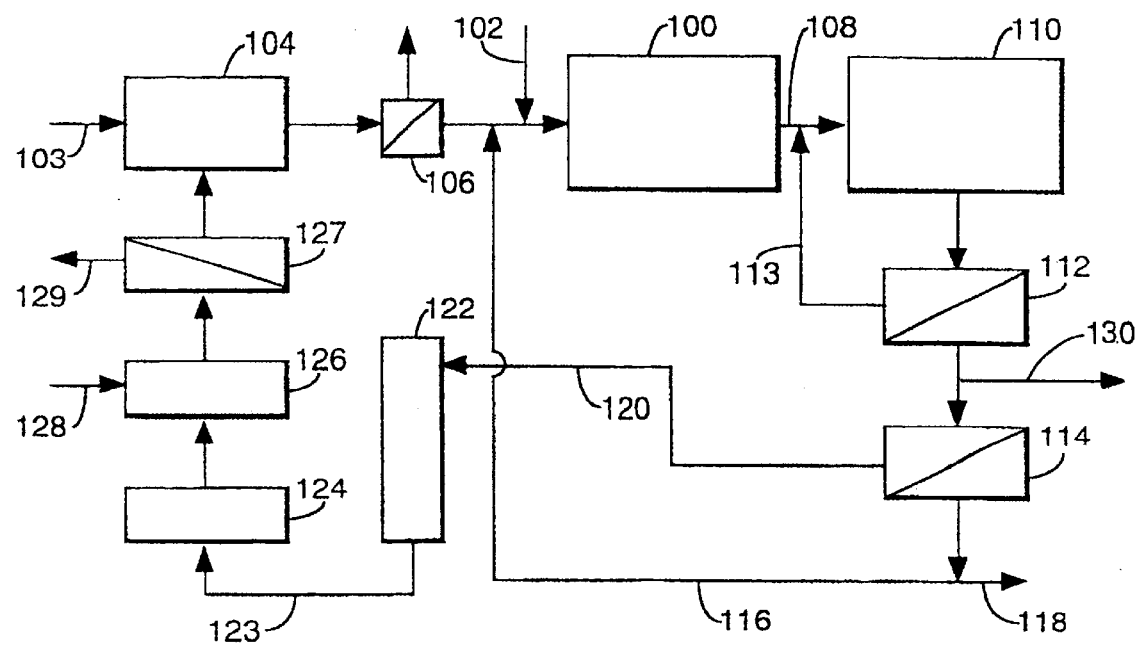
FIG. 3 illustrates a further embodiment of effluent treatment plant also employing anaerobic digestion.

Referring now to FIG. 3, in this embodiment the effectiveness of the alkali recovered from the reverse osmosis membrane treatment is improved in a number of respects. The effluent treatment plant comprises an anaerobic treatment unit 100 to which waste waters from a terephthalic production plant are supplied; these waste waters are depicted collectively by line 102 and, as previously described in connection with FIG. 1, may comprise for example aqueous mother liquor from the purification process (usually the major component) and spent caustic wash water employed in washing duties on the plant. The anaerobic treatment facility also receives filtrate from catalyst recovery facility 104 following precipitation and recovery of catalyst metals via filter 106. The catalyst recovery facility 104 receives oxidation residues via line 103. The catalyst recovery process may be as described in connection with FIG. 2.

Following anaerobic treatment, the treated liquor is passed via line 108 to aerobic digestion unit 110 and the treated stream (reduced COD stream) from unit 110 is passed to microfiltration unit 112, from which the filtrate is supplied to reverse osmosis (RO) membrane stage 114. The units 110, 112 and the RO membrane stage 114 function in generally the same manner as their counterparts described in relation to FIG. 1. The backwash from the microfiltration unit 112 is recycled via line 113 to the aerobic unit 110. A purge is taken from the reduced COD stream prior to contacting the RO membrane 114. The permeate from RO membrane stage 114 is in part recycled via line 116 to the anaerobic unit 100 and in part recycled via line 118 (and if necessary demineralisation plant) for re-use elsewhere in the plant. The permeate typically comprises at least 70% of the feed water supplied to the anaerobic unit 100. The retentate, which contains sodium and bicarbonate and typically has a pH of the order of 7.6, is ultimately employed in controlling the pH of the liquors supplied to the anaerobic unit 100 and hence to the aerobic unit 110.

While part of the retentate may be supplied directly to the anaerobic unit 100 in order to adjust pH for compatability with the anaerobic and aerobic organic digestion processes, in FIG. 3 the major part, preferably the entire amount of, of retentate is supplied via line 120 to the offgas scrubber 122 for use in scrubbing bromine and HBr from the oxidation offgas stream as described previously and substantially eliminates the need to supply fresh caustic soda for this duty. Although the offgas will contain $CO_2$, the partial pressure of $CO_2$ present in the retentate will be low and consequently contact with the offgas will result in stripping of $CO_2$ from the retentate during the scrubbing process thereby raising the pH of the retentate liquor, to about 8.9. The retentate-derived bottoms liquor recovered from the offgas scrubber 122 is passed via line 123 to an air stripper 124 which serves to remove further $CO_2$ from the liquor raising its pH still further, e.g. to 9.3. Because the catalyst precipitation step typically requires a pH of at least 7.5, the removal of a substantial proportion of the $CO_2$ present in the retentate in this way, ensures that this pH requirement can be met with minimum usage of fresh caustic soda.

Following scrubbing the retentate-derived liquor, which at this point will comprise a mixture of bicarbonate and carbonate, is passed to a buffer tank 126 to which caustic soda may be added via line 128 if needed. Prior to use as a neutralising agent in the catalyst recovery facility 104, the alkali is passed to filtration unit 127 in order to remove, via line 129, materials such as $CaCO_3$ and transitional metal carbonates/hydroxides which will tend to be precipitated at the high pH levels prevailing following recovery of the retenate-based scrubbing liquor. Following use in the catalyst recovery facility 104 and recovery of the filtrate from the filter 106, the alkali values contributed by the retentate are employed in adjustment of pH of the aqueous waste waters supplied via line 102 thereby using the retentate indirectly (i.e. via off-gas scrubbing and catalyst recovery) to make this adjustment as opposed to directly as in the embodiments of FIGS. 2 and 3. In the embodiment of FIG. 3, the permeate is also used in controlling the pH of the feed to the anaerobic unit and avoids the introduction of mineral acids such as HCl into the anaerobic unit 100 which would otherwise require an equivalent increase in caustic usage and also tends to increase the background levels of dissolved solids. Thus, the low impurity product of the RO membrane stage 114 is split with most being used for dilution of the largely acidic waste waters supplied via line 102 and the balance being supplied to demineralised water plant via line 118.

A purge may be necessary from the effluent treatment plant to balance the ingress of "involuntary" sodium, i.e. that which enters the effluent treatment plant from fresh caustic soda used for washing operations etc on the plant. In the embodiment of FIG. 3, the purge is taken immediately upstream of the RO membrane stage 114 via line 130. The volume of the purge stream may be set to secure a sodium concentration and overall composition within prescribed regulatory limits.

Although in the illustrated embodiments, reverse osmosis membrane technology is employed, it will be appreciated that the embodiments may instead be implemented using evaporative techniques, e.g. multi-effect evaporation, in place of reverse osmosis membrane separations.

From the foregoing, it will seen the embodiments described allow the import of raw water into a process for the production of purified terephthalic acid to be reduced significantly while at the same time reducing the aqueous caustic soda inventory by making use of recovered sodium salts, particularly sodium carbonate and/or bicarbonate, for in at least some of those duties where aqueous caustic soda would otherwise be used. Moreover, the levels of COD and sodium discharged can be reduced substantially. Additionally the components employed in the process are readily retrofittable to existing terephthalic acid production plant.

What is claimed is:

1. A process for the treatment of an effluent stream containing water and an organic acid species which is a stronger acid than carbonic acid, comprising:
    adding an alkaline medium to increase the pH of the effluent stream;
    subjecting the effluent stream to oxidation treatment to convert the organic acid species to carbon dioxide, water and carbonate and/or bicarbonate ions;
    separating the oxidised effluent stream into a concentrated aqueous stream rich in (bi)carbonate ions and cationic species derived from said alkaline medium and a depleted aqueous stream which is substantially free of said (bi)carbonate ions and said cationic species; and
    recycling the concentrated stream for direct or indirect use as said alkaline medium.

2. A process for the production of an aromatic carboxylic acid by the oxidation of a precursor thereof, comprising feeding at least one organic acid-containing effluent water stream generated in the course of operating the process to a effluent water treatment plant in which the pH of the stream is adjusted by the addition of an alkaline medium and is subjected to oxidation treatment to decompose its organic components, separating the oxidised stream into a depleted stream comprising water having low organics content and a concentrated stream comprising water from said stream, cationic species derived from the alkaline medium and (bi)carbonate ions generated in the course of oxidation of the organics, at least part of the concentrated stream being recycled for direct or indirect use in said adjustment of the pH of the effluent water stream and, optionally, at least part of the depleted stream being recovered and re-used in one or more water-consuming applications within and/or associated with the production process.

3. A process as claimed in claim 1 or 2 in which separation of the oxidised stream into the concentrated and depleted streams is effected by contacting the oxidised stream with at least one reverse osmosis membrane.

4. A process as claimed in claim 1 or 2 in which separation of the oxidised stream into the concentrated and depleted streams is effected by an evaporative technique.

5. A process as claimed in claim 1 or 2 in which the alkaline medium contains an alkali metal.

6. A process for the production of an aromatic carboxylic acid by the liquid phase oxidation of a precursor thereof, comprising:
    feeding at least one impurity-containing effluent water stream from the process to a effluent water treatment plant including oxidation treatment in which a substantial proportion of the organics present in the effluent water stream is oxidised to carbon dioxide, water and (bi)carbonate ions;
    supplying the treated stream containing suspended solids to a solids-liquid separation stage to produce a solids-rich stream comprising suspended solids and water from said treated stream and a substantially solids-free stream comprising water and dissolved impurities;
    supplying the solids-free stream from the solid-liquid separation stage to a reverse osmosis membrane stage to produce a permeate stream having a low impurity content and a retentate stream rich in impurities; and
    recycling the retentate stream at least in part for direct or indirect use in adjusting the pH of the effluent water stream prior to and/or during oxidation thereof and, optionally, recycling the permeate stream, the solids-free stream and/or the solids-rich stream at least in part for re-use in one or more water-consuming applications within and/or associated with the production process.

7. A process for the production of an aromatic carboxylic acid, comprising:
    effecting liquid phase oxidation of a precursor of said aromatic carboxylic acid in an aliphatic carboxylic acid solvent in the presence of a heavy metal catalyst system;
    supplying a slurry of the resulting aromatic carboxylic acid crystals in solvent-based mother liquor to a solids-liquid separation section to separate said crystals of crude aromatic carboxylic acid from said solvent-based mother liquor;
    dissolving the crude acid crystals in aqueous medium;
    hydrogenating the resulting solution to reduce the impurity content of the aromatic carboxylic acid;
    separating purified crystals of the aromatic carboxylic acid from aqueous-based mother liquor;
    adjusting the pH of at least part of the aqueous-based mother liquor by the addition of alkaline medium thereto;
    following pH adjustment subjecting said aqueous-based mother liquor in treated or untreated form to an organics digestion process to produce a reduced COD aqueous stream containing suspended solids and dissolved species including (bi)carbonate ions and cationic species derived from said alkaline medium;
    processing said reduced COD aqueous stream to separate the same into a concentrated stream comprising a minor fraction of the water from said reduced COD aqueous stream and containing substantially all of the impurities constituted by said dissolved species, including (bi)carbonate ions, and a depleted stream which comprises a major fraction of the water from the reduced COD stream and which is substantially free of said impurities; and
    recycling at least part of said depleted stream for direct or indirect use in said pH adjustment and, optionally, recycling at least part of the depleted stream for re-use in one or more water-consuming units within and/or associated with the production plant.

8. A process as claimed in claim 7 further comprising recycling the recovered aliphatic acid solvent-based mother liquor in part to the oxidation reaction after taking a purge therefrom; concentrating the solvent-based mother liquor purge in a solvent recovery zone to produce a residue containing organics and catalyst metal; dissolving the residue in water and treating the same to recover catalyst metals by precipitation and separation from the aqueous medium; and supplying the aqueous medium remaining after recovery of the catalyst metals to said organic digestion process along with said aqueous-based mother liquor.

9. A process as claimed in claim 8 in which at least part, preferably at least a major part of said concentrated stream is employed in the catalyst recovery process and the aqueous medium remaining after recovery of the catalyst metals is used in the adjustment of the aqueous-based mother liquor supplied to the organics digestion process.

10. A process as claimed in claim 8 or 9 in which at least part of the concentrated stream is employed in effecting scrubbing of off-gas derived from the liquid phase oxidation reaction.

11. Plant for the production of an aromatic carboxylic acid, comprising:

an oxidation zone in which a crude acid is first produced by the liquid phase oxidation of a precursor of the acid in an aliphatic carboxylic solvent in the presence of a heavy metal catalyst system;

a solids-liquid separation section in which crystals of the crude aromatic carboxylic acid are separated from oxidation zone mother liquor comprising mainly said aliphatic carboxylic acid solvent;

a purification zone in which the crude acid crystals are dissolved in aqueous medium and the resulting aqueous solution is hydrogenated to reduce the impurity content of the aromatic carboxylic acid;

a pure solids-liquid separation section in which purified crystals of the aromatic carboxylic acid are separated from the purification zone aqueous mother liquor;

an organics digestion stage receiving at least part of said purification zone mother liquor in treated or untreated form and producing a reduced COD aqueous stream containing suspended solids and dissolved species including (bi)carbonate ions;

means for adjusting the pH of the purification zone mother liquor by addition of alkaline medium prior to, or during, treatment within the organics digestion stage;

a solids-liquid separation stage receiving said reduced COD stream and separating the same into a solids-rich stream comprising a minor fraction of the water from said reduced COD stream together with suspended solids and a substantially solids-free stream containing the major fraction of the water from said reduced COD stream and dissolved species including (bi)carbonate ions;

a reverse osmosis membrane stage for receiving said solids-free stream and producing a retentate stream comprising a minor fraction of the water from said solids-free stream and containing substantially all of the impurities constituted by said dissolved species, including (bi)carbonate ions and cationic species from said alkaline medium, in the solids-free stream and a permeate stream comprising the major fraction of water and residual dissolved species from the solids-free stream; and means for recycling at least part of the retentate stream directly or indirectly to said pH adjusting means.

12. Plant as claimed in claim 11 including means for feeding the recovered oxidation zone mother liquor in part as a recycle stream to the oxidation zone and in part as a purge stream to a solvent recovery zone in which the purge stream is concentrated to produce a residue containing organics and catalyst metal; means for dissolving the residue in water and recovering catalyst metals from the solution to leave an organics-containing aqueous stream; and means for feeding said aqueous stream derived from residue treatment to the solids-liquid separation stage for producing said reduced COD stream.

13. Plant as claimed in claim 11 or 12 in which the solids-liquid separation stage includes a microfiltration membrane stage.

* * * * *